United States Patent [19]

Kelleghan

[11] Patent Number: 4,503,254

[45] Date of Patent: Mar. 5, 1985

[54] PROCESS FOR MAKING BIS(HALOPHENYL)HEXAFLUOROPROPANES

[75] Inventor: William J. Kelleghan, Whittier, Calif.

[73] Assignee: Hughes Aircraft Company, El Segundo, Calif.

[21] Appl. No.: 361,281

[22] Filed: Mar. 24, 1982

[51] Int. Cl.$^3$ .................... C07F 9/53

[52] U.S. Cl. .................... 568/14; 570/144; 570/184

[58] Field of Search .................... 568/14; 570/144, 184

[56] References Cited

U.S. PATENT DOCUMENTS 3,017,440 1/1962 Entemann .................... 570/144
3,284,518 11/1966 Ayers et al. .................... 570/144
3,895,074 7/1975 Mrowca .................... 568/14
4,092,363 5/1978 Staendeke et al. .................... 568/14

FOREIGN PATENT DOCUMENTS 276949 10/1970 U.S.S.R. .................... 568/14
819114 8/1978 U.S.S.R. .................... 568/14

OTHER PUBLICATIONS

Chemical Abstracts 82 139702s (1975).
Kosolapoff, Organic Phosphorus Compounds, Wiley Intersc. N.Y., vol. 3, pp. 369, 477, 483 (1972).
Fleissner, Chem. Ber. 13, p. 1665 (1880).
Chemical Abstracts, 80, 28170f (1974).
Chemical Abstracts, 77, 5842a and 63551r (1972).
Chemical Abstracts, 68, 12278p (1968).
Chemical Abstracts, 60, 741d (1960).

*Primary Examiner*—Helen M. S. Sneed
*Attorney, Agent, or Firm*—A. W. Karambelas

[57] ABSTRACT

A new process for preparing diphenyl derivatives of hexafluoropropane containing halogen substituents on the phenyl rings and new halogen-substituted diphenyl derivatives of hexafluoropropane prepared thereby are disclosed. The new compounds of this invention are useful as intermediates for the synthesis of high temperature polymer systems.

4 Claims, 1 Drawing Figure

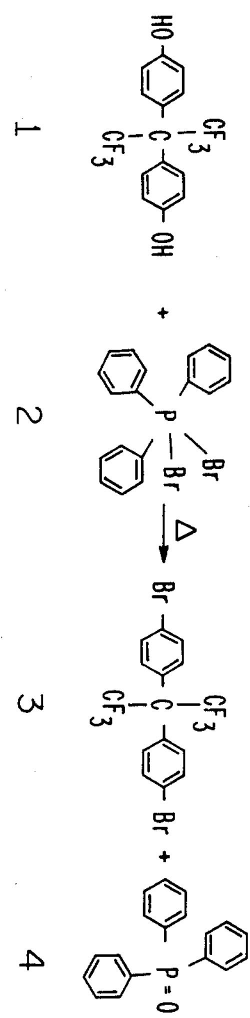
1
2
3
4
HO
OH
$CF_3$
C
P
Br
P=O

PROCESS FOR MAKING BIS(HALOPHENYL)HEXAFLUOROPROPANES

TECHNICAL FIELD

This invention relates, generally, to the synthesis of aromatic hexafluoropropane derivatives and more particularly to the synthesis of bis(halophenyl)hexafluoropropanes.

BACKGROUND OF THE INVENTION

1. Field of the Invention

It has been determined that continued problems in processing high temperature resistant aromatic heterocyclic polymer systems may be lessened by the incorporation of hexafluoroisopropylidene (6F) units in the polymer backbone structure. These 6F units tend to lower the glass transition temperature (Tg) of polymers prepared therewith and thus improve their melt characteristics. In addition, 6F units within a polymer chain prohibit extensive conjugation of aromatic moieties, thereby providing good electric insulation characteristics for the end product resins. Such lack of conjugation also obliterates UV-visible chromophores, thus allowing end product polyimides to appear colorless and to resist photochemical degradation.

Key monomers for the synthesis of thermally stable high temperature resins containing 6F groups have been prepared from commercially available 2,2-bis(4-hydroxyphenyl)hexafluoropropane, commonly known as Bisphenol AF. However, because of the resistance of the hydroxy functions on Bisphenol AF to replacement by direct chemical modification, the availability of such monomers is severely limited to monomers having substituents which are less reactive than halogen substituents.

Diphenyl derivatives of hexafluoropropane have proven to be useful intermediates in the synthesis of thermally stable resins for use in high temperature structural composites. Halogenated 2,2-diphenyl derivatives of hexafluoropropane can be predicted to be particularly useful in that the halogen substituents will render the derivative more reactive and thus easier to utilize in preparing high temperature resins. 2,2-Bis(4-bromophenyl)hexafluoropropane is a novel species of this class of compounds that has a great potential for use as an intermediate in the synthesis of high temperature resins for colorless coating applications. Therefore, this invention is directed to the provision of novel bis(halophenyl)hexafluoropropane compounds and an improved process for making bis(halophenyl)hexafluoropropane compounds.

2. Description of the Prior Art

Bisphenols in general and 2,2-bis(4-hydroxyphenyl)-hexafluoropropane (Bisphenol AF) in particular have been used by others as starting materials for the synthesis of intermediates used in the preparation of high temperature resins. These materials are commercially available. However, the transformation of the hydroxy substituents found on the phenylene rings of these bisphenols into other substituents is difficult because phenols in general are inert towards direct displacement reactions. In the case of Bisphenol AF, which contains the inductively electron withdrawing hexafluoroisopropylidene (6F) group in addition to the relatively inert hydroxyl groups, the synthesis of intermediates containing halogen substituents on the phenylene ring is particularly difficult and inefficient.

Attempts to prepare 2,2-bis(4-bromophenyl)hexafluoropropane using phosphorus pentabromide as a brominating agent yield an intractable product mixture, as reported by Dr. K. L. Paciorek, et al. of Ultrasystems, Incorporated, of Irvine, Calif.; see NASA Report No. CR-159403 entitled "Synthesis of Perfluoroalkylene Diamines" that was submitted under NASA Lewis Research Center Contract NAS3-20400 August 1978. It can be concluded from this work that there are no suitable prior art methods for preparing halogen substituted diphenyl derivatives of hexafluoropropane.

Therefore, there is still a need for an efficient process for preparing 2,2-diphenyl derivatives of hexafluoropropane having halogen substituents thereon and there is particularly a need for para-substituted 2, 2-diphenyl derivatives of hexafluoropropane.

SUMMARY OF THE INVENTION

In seeking to provide 2,2-bis(4-bromophenyl)hexafluoropropane for use in the synthesis of high temperature resins such as polyether, polyarene, or polyimide polymers, a novel exchange process has been discovered for producing meta- and para-substituted 2,2-bis(-halophenyl)hexafluoropropanes which avoids the disadvantages of prior art processes while retaining most, if not all, of the advantages of prior art processes. As a consequence of this discovery, I have made novel reactive monomers comprising two phenylene rings linked together by a hexafluoroisopropylidene group where each of said rings bears a single halogen substitutent thereon.

The process of this invention entails the formation of a reaction mixture by blending a triphenylphosphine dihalide with a 2,2-bis(hydroxyphenyl)hexafluoropropane and subsequently heating the reaction mixture to at least 280° C. to promote an overall hydroxy-to-halogen exchange reaction which yields the desired halogen-substituted monomer.

It is therefore one purpose of this invention to provide halogen-substituted 2,2-diphenylhexafluoropropanes for use in the synthesis of high temperature resins.

A further purpose of this invention is to provide an efficient and simple process for preparing halogen substituted 2,2-diphenyl derivatives of hexafluoropropane.

A still further purpose of this invention is to provide 2,2-bis(4-bromophenyl)hexafluoropropane in high yields at a reduced cost.

That the above stated purposes, and other worthwhile advantages, have been accomplished will be apparent upon reference to the following detailed description of the invention.

DETAILED DESCRIPTION OF THE INVENTION

As a result of studies intended to overcome the shortage of suitable monomers containing 6F units, it has been discovered that triphenylphosphine dihalides will effect the displacement of the hydroxy substituents on Bisphenol AF when a mixture of the two reactants is heated above 280° C. to thereby yield a 2,2-bis(4-halophenyl)hexafluoropropane. The experimental procedure is simple and can be easily monitored by the evolution of gases from the reaction mixture as it is heated; thus the process can be easily modified for commercial operations.

Triphenylphosphine dibromide has preferably been utilized in this process as a brominating agent to displace the hydroxy functions on Bisphenol AF, however, other triphenylphosphine dihalides appear to be equally suitable. Included among these compounds are triphenylphosphine dichloride and triphenylphosphine diiodide.

The preferred reaction proceeds according to the following sequence:

Referring to the above reaction sequence, Reactant (1) is added to a slurry of Reactant (2) in a solvent under an inert atmosphere such as argon to exclude oxygen from the reaction mixture. Nitrogen may be used in lieu of argon. However, argon is preferred because of its greater density. Although not absolutely necessary, intimate and complete mixing of reagents promotes rapid and complete reaction. For our purposes, we prefer to use dichloromethane as a mixing solvent. However, other low boiling polar solvents, such as acetonitrile and chloroform may be utilized to form a reactant mixture. The resulting mixture is then heated, from 2 to 6 hours depending on the temperature employed, in a molten metal bath and agitated. The triphenylphosphine oxide byproduct (4) of the reaction is separated from the target compound (3) by conventional chemical processes such as solvent extraction, liquid chromatography, and distillation.

The preparation of 2,2-bis(4-bromophenyl)hexafluoropropane by the method described above facilitates the synthesis of other halogen-substituted diphenyl derivatives having 6F groups therein, which were previously unavailable, by direct halogen exchange reactions. Thus, compounds whose structures are

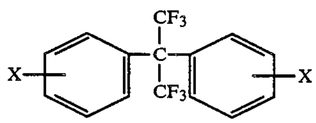

where X is fluorine, chlorine or iodine may also be prepared. These compounds may be produced by any number of halogen exchange reactions known in the prior art, such as decomposition of organometallics or reaction with inorganic halogen-containing salts, in yields dependent upon the method used.

While it is clear that both para- and meta-substituted isomers of the bromine derivative of hexafluoropropane may be prepared via the above-described process, in the case of the meta isomer another synthetic route is available which ultimately yields the meta-bromo derivative via a "Sandmeyer" reaction. In this process 2,2-Bis(3-bromophenyl)hexafluoropropane, a meta-substituted isomer, was prepared by my coworkers and me using the "Sandmeyer" reaction following a sequence of several steps to obtain 2,2-bis(3-aminophenyl)hexafluoropropane from Bisphenol AF. However, the overall yield of the meta species from Bisphenol AF was low and poorly suited for commercial operations. This work is described in an article entitled "Synthesis of Polymer Intermediates Containing the Hexafluoroisopropylidene Group Via Functionalization of 2,2-Diphenylhexafluoropropane" in the Journal of Polymer Science, Polymer Chemistry Edition Vol. 20, pages 2381 to 2393, 1982.

Specific examples of the above-described invention are shown below.

EXAMPLES

Example I

Bromination of Bisphenol AF

To a slurry of triphenylphosphine dibromide (0.2 mole) in dichloromethane (250 ml) under argon was added 2,2-bis(4-hydroxyphenyl)hexafluoropropane (0.1 mole). The solvent was removed by distillation to leave a solid reaction mixture, and the reaction mixture (contained in a flask) was placed in a molten metal bath at 350° C. for two hours. The reaction mixture was cooled to 100° C. and poured into a flask. A resulting solid within the flask was washed three times with 300 ml portions of hexane and filtered to remove unwanted reaction by-products. The resulting hexane solution of the product was washed with 20% sodium hydroxide and deionized water. The solution was then dried over anhydrous magnesium sulfate and passed down a short alumina column. The hexane was removed from the solution and the resulting semi-solid was distilled to produce a 76% yield of the product 2,2-bis(4-bromophenyl)hexafluoropropane which is a high yield for reactions of this nature.

Physical Data:

ir (KBr) 1590(w), 1495(m), 1245(s), 1208(s), 1171(s), 818(m) $cm^{-1}$.

nmr ($CDCl_3$) δ 7.61, 7.46, 7.30, 7.15 ppm (aromatic, para-substitution pattern)

| | | C | H | F | Br |
|---|---|---|---|---|---|
| Anal. | Calc. | 38.99 | 1.74 | 24.67 | 34.59 |
| $C_{15}H_8F_6Br_2$ | Found | 39.03 | 1.75 | 24.70 | 34.68 |

Example II

Chlorination of Bisphenol AF

To a slurry of triphenylphosphine dichloride (0.2 moles) in dichloromethane (250 ml) under argon is added 2,2-bis(4-hydroxyphenyl)hexafluoropropane (0.1 mole). The solvent is removed by distillation to form an essentially solid reaction mixture in the reaction vessel. The reaction vessel is heated in a molten metal bath to form a molten reaction mixture and the mixture agitated for approximately four hours before cooling to obtain a solid reaction product. The resulting solid is dissolved in dichloromethane and washed first with dilute sodium hydroxide and second with deionized water. The resulting organic fraction is collected and purified passing it through a silica gel chromatographic column using hexane as the eluting solvent. The hexane is removed from the eluate with a rotary evaporator to yield 2,2-bis(4-chlorophenyl)hexafluoropropane.

Example III

Preparation of 2,2-bis(4-fluorophenyl)hexafluoropropane

In 200 ml of dry dimethylsulfoxide, 4.62 grams (0.01 moles) of 2,2-bis(4-bromophenyl)hexafluoropropane is dissolved to form a solution. Anhydrous potassium fluoride (1.28 grams, 0.022 mole) and 0.1 g of 18 Crown-6 catalyst (sold by Aldrich Chemical Co., Milwaukee, Wis.) is added to the solution under argon to form a reaction mixture. The mixture is heated for approximately eight hours at 175°-80° C. before being allowed to cool. The resulting product is filtered, concentrated, taken up in dichloromethane, washed with water, and finally concentrated to yield the crude product, 2,2-bis(4-fluorophenyl)hexafluoropropane.

Example IV

Preparation of 2,2-bis(4-iodophenyl)hexafluoropropane

To a solution of 4.62 grams (0.01 mole) of 2,2-bis(4-bromophenyl)hexafluoropropane in 50 ml of anhydrous ethyl ether under argon at 0° C., is added dropwise 13.7 ml (0.022 mole) of a 1.6 molar solution of n-butyllithium in hexane. The mixture is stirred at 25° C. for two hours and cooled to 0° C. A solution of 2.8 grams iodine in 50 ml of anhydrous ethyl ether is added dropwise and allowed to stir for approximately 16 hours at 25° C. The resultant product is then washed sequentially with 200 ml of water, 200 ml of 20% aqueous sodium bisulfite, 200 ml of saturated sodium bicarbonate solution, and 200 ml of water. The resulting organic phase is separated from the aqueous phase, dried over magnesium sulfate, filtered, and concentrated to yield the product 2,2-bis(4-iodophenyl)hexafluoropropane.

INDUSTRIAL APPLICATION

The process disclosed above, and the halogen-substituted, 2-2-diphenyl derivatives of hexafluoropropane prepared by the process, may be used in the synthesis of high temperature polymer systems such as the polyethers, polyarenes, and polyimides. These systems are useful as adhesives, structural resins and potting compounds. Colorless resins prepared from these monomers are useful as protective coatings.

Having disclosed the nature of my invention and having provided teachings to enable others to make and use my invention, my claims may now be understood as follows:

What is claimed is:

1. A process for preparing a reactive monomer whose structure is

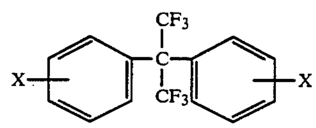

where X is a halogen comprising the steps of:

forming a reaction mixture by blending a triphenylphosphine dihalide reactant with a 2,2-bis(hydroxphenyl)hexafluoropropane reactant; and heating said mixture to at least 280° C. to promote a reaction between said reactants as evidenced by the evolution of a gaseous by-product, thereby forming a solid mixture of said monomer and triphenylphosphine oxide which may be subsequently separated to give high yields of said monomer.

2. The process of claim 1 wherein said mixture is first formed from a slurry of said dihalide in a low boiling hydrocarbon solvent to which said hexafluoropropane is added under an inert atmosphere.

3. The process of claim 2 where said solvent is stripped from said mixture by distillation and said mixture is subsequently heated to 350° C. to promote said reaction.

4. The process of claim 1 where said dihalide is triphenylphosphine dibromide and said hexafluoropropane is Bisphenol AF.

* * * * *